United States Patent [19]

Kawahara et al.

[11] 4,016,651
[45] Apr. 12, 1977

[54] DEVICE FOR IMPLANTING AN ARTIFICIAL ENDOSSEOUS ELEMENT OF CERAMICS AND AN IMPLANT METHOD FOR USE OF THE DEVICE

[75] Inventors: Haruyuki Kawahara, Moriguchi; Masaya Hirabayashi, Yokaichi, both of Japan

[73] Assignee: Kyoto Ceramic Co., Ltd., Kyoto, Japan

[22] Filed: Feb. 18, 1975

[21] Appl. No.: 550,186

[30] Foreign Application Priority Data

Sept. 25, 1974 Japan .............................. 49-110730

[52] U.S. Cl. ................................................ 32/10 A
[51] Int. Cl.² .................................... A61C 13/00
[58] Field of Search ................................... 32/10 A

[56] References Cited

UNITED STATES PATENTS

| | | | |
|---|---|---|---|
| 2,210,424 | 8/1940 | Morrison | 32/10 A |
| 3,082,525 | 3/1963 | Christensen | 32/10 A |
| 3,435,526 | 4/1969 | Brancato | 32/10 A |
| 3,579,831 | 5/1971 | Stevens | 32/10 A |
| 3,664,022 | 5/1972 | Small | 32/10 A |
| 3,776,744 | 12/1973 | Clendenen | 106/73.4 |

*Primary Examiner*—Robert Peshock
*Attorney, Agent, or Firm*—Spensley, Horn & Lubitz

[57] ABSTRACT

This invention is directed to a device for implanting an artificial endosseous element of ceramics in the fields of dentistry, oral surgery and orthopedics, comprising an implant screw pin and more than one nut element in combination with said screw pin primarily for securely holding said screw pin in a bone structure after implantation thereof. This invention is also directed to an implant method for use of such device.

22 Claims, 6 Drawing Figures

DEVICE FOR IMPLANTING AN ARTIFICIAL ENDOSSEOUS ELEMENT OF CERAMICS AND AN IMPLANT METHOD FOR USE OF THE DEVICE

BACKGROUND OF THE INVENTION

1. Field of the Invention

This invention relates to a device for implanting an artificial endosseous element of ceramics in the fields of dentistry, oral surgery and orthopedics, and to a method for implanting such device.

2. Description of the Prior Art

In accordance with the recent trand of development of bio-engineering, implantation of artificial bio-material into the bone tissue of a living body has become popular. For instance, a dental implantation technique has been developed, wherein in order to compensate for the loss of natural teeth, an artificial tooth or implant is implanted or inserted in the endosseous or subperiosteal portion of the jaw as a substitute for a clasp abutment tooth of a cantilevered bridge or an abutment tooth of a fixed bridge. The artificial tooth or teeth thus implanted by the implantation technique is called an implant crown, an implant bridge or an implant denture.

As for the type of the endosseous implant in the fields of dentistry and oral surgery, the pin, blade and screw variety is well known. A screw implant has, on the circumference of an implant screw pin ($i_0$), as shown in FIGS. 5 and 6, a screw (10) for threading into a jaw bone ($b$). The implant screw pin ($i_0$) is screwed in a tapped hole (50) provided in the jaw bone. The tapped hole (50) can readily be made to correspond to the screw (10) to be implanted in the jaw bone ($b$). After the implant screw pin ($i_0$) is implanted in the jaw bone ($b$), an artificial tooth ($t$) is fixed to an upper portion (20) of the implant screw pin ($i_0$) by means of an adhesive compound (40). Since the formation of the tapped hole in the bone tissue may cause some destruction of the bone tissue or pain to the patient, the pitch of the thread in the tapped hole (50) is designed to be comparatively large. In response thereto the pitch of the screw (10) of the implant screw pin ($i_0$) is made large.

Accordingly, when the implant screw pin ($i_0$) is screwed in the bone structure, a substantial clearance is formed between the screw (10) and the tapped hole (50) and under these conditions, if repeated biting stress is concentrated to a lower portion ($t_2$) of the artificial tooth ($t$) connected to a portion (20) (tool-attaching portion) above the implant screw pin ($i_0$), the connection between the implant screw pin ($i_0$) and the jaw bone ($b$) may become loose. The implant screw pin ($i_0$) may then become infirm or unstable, and a pocket ($p$) may be formed between the gingival tissue and the implant screw pin ($i_0$). This condition may not only prevent the growth of the tissues surrounding the implant screw pin ($i_0$), but also it may cause some bone atrophy. The pocket ($p$) may become enlarged as a result of bone atrophy, whereupon the implant screw pin ($i_0$) becomes more unstable even to the point of causing the implant screw pin ($i_0$) to drop out of hole (50) thus reducing the pocket ($p$) to a nest of bacilli which will infect the patient.

BRIEF SUMMARY OF THE INVENTION

Therefore, one of the objects of the present invention is to provide a device for implanting an artificial endosseous element which has excellent stability under biting stress.

Another object of the present invention is to provide a simplified method for implanting an artificial endosseous element or device.

Still another object of the present invention is to provide the device for implanting an artificial endosseous element in which the surrounding tissues will grow well without formation of a pocket.

Yet still another object of the present invention is to provide the device for implanting an artificial endosseous element which will endure a long time after implantation.

These and other objects and advantages will become more apparent from the following description of embodiments.

BRIEF DESCRIPTION OF THE DRAWINGS

Two preferred embodiments with the examples of the implant in the fields of dentistry and oral surgery of the invention are described hereinafter with reference to the accompanying drawings in which.

DETAILED DESCRIPTION OF THE PREFERRED EMBODIMENT

Figure 1:
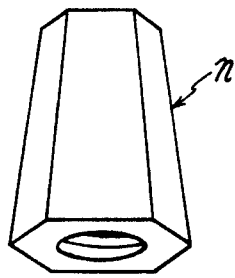
FIG. 1 is a perspective view of a device for implanting an artificial endosseous element including an implant screw pin and a nut element according to the first embodiment of the invention.
Figure 2:
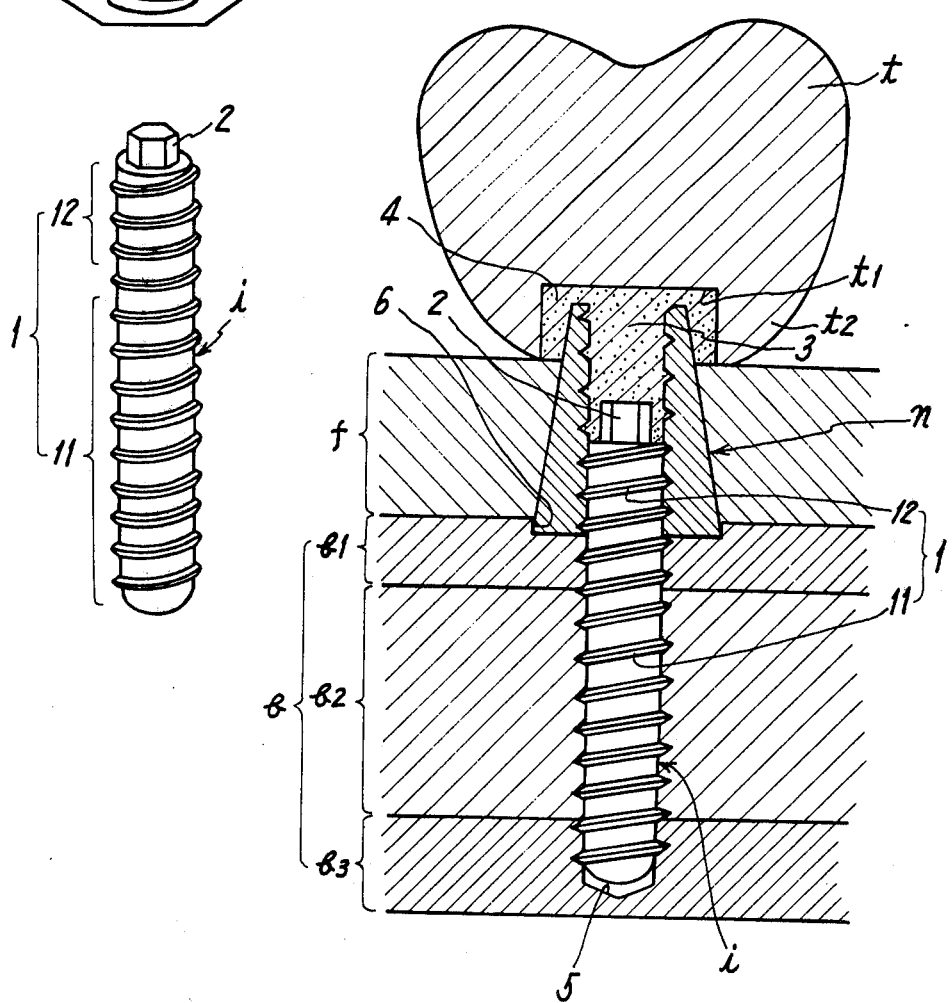
FIG. 2 is a cross-sectional view showing the implantation of the artificial endosseous element shown in FIG. 1.

As is apparent from FIGS. 1 and 2, an implant screw pin ($i$) according to the first embodiment is provided, on the external circumference thereof, with a screw (1) in which a portion (11) (hereinafter referred to as a main screw portion) is adapted to be threaded in the jaw bone ($b$) and in which a portion (12) (hereinafter referred to as a protruded screw portion) is adapted to be protruded from the upper surface of the jaw bone ($b$). The screw (1) is usually formed by a single screw thread. The implant screw pin ($i$) is provided at the top thereof with a wrench-attaching portion (2) having a hexagonal pillar shape. A nut element ($n$) is threaded in the above-mentioned portion (12) of the implant screw pin ($i$) so that the underside of the nut element ($n$) may be tightly connected to the upperside of the jaw bone ($b$) and the artificial tooth ($t$) may be fixed securely into the upper portion of the nut element ($n$).

In the drawing, the circumference of the nut element ($n$) is shown as is tapered with respect to the upward direction. This for the purpose of easy operation in pressing or fixing the artificial tooth by striking thereof from the upperside into the top portion of the nut element ($n$). As for the material of the implant screw pin ($i$) and the nut element ($n$), ceramic compositions of matter have better compatibility with the tissues of a living body than metal and are thus preferred. However, among ceramic compositions of matter, alumina ceramics is the most preferable. Furthermore, the use of alumina ceramics of the composition partly disclosed in our copending application, Ser. No. 524,557, is preferable by the following reasons. Namely, according to our copending application concerning a burnt ceramics composition of matter for a ceramic implant adapted for use in the bone tissue of a living body, at the final composition range after burning thereof, the ceramics composition consists of 95 to 50% of $Al_2O_3$ and 5 to 50% of more than one compound selected from the group consisting of $ZrO_2$, $La_2O$ and $Y_2O_3$ and preferably consists, at the final composition range after burning thereof, of 90 to 80% of $Al_2O_3$ and 10 to 20% of more than one compound selected from the group consisting of $ZrO_2$, $La_2O$ and $Y_2O_3$. The above specified alumina ceramics composition of matter has good mechanical strength and resistance to the external forces imparted by the implant pin or a nut element, for instance, to the repeated biting stress between the implant pin or the nut element and the artificial tooth. The alumina ceramics composition of matter is also opaque to X-rays so that the position of the implant pin or the nut element can be pictured in white on the X-ray dry plate picture thereby proving advantageous when judging the progressive change of the tissues surrounding the implant pin or the nut element.

The manner of prosthesis of the artificial tooth ($t$) in use of an implant screw pin ($i$) and a nut element ($n$) embodied in the first embodiment of the present invention is described hereinafter by way of FIG. 2. At first, a gingival tissue ($f$) of the prosthesis section is incised and a tapped hole (5), which corresponds with the main screw portion (11) to be threaded in the bone structure, is provided. Next, a wrench is attached to the wrench-attaching portion (2) of the implant screw pin ($i$) to rotate the portion (2) thereby screwing the main screw portion (11) into the tapped hole (5) until the lower end of the main screw portion (11) reaches a hard tissue ($b_3$) of the lower side of the jaw bone ($b$). Then the implant screw pin ($i$) is implanted in the jaw bone ($b$), leaving the top portion of the screw ($l$) protruding above the jaw bone ($b$) from the upper surface thereof in order to present the protruded screw portion (12). Under the conditions as described above, there exists a substantial clearance in the respective threads of the main screw portion (11) and the tapped hole (5). Thus the implant screw pin ($i$) cannot be securely held in the jaw bone ($b$) and is somewhat insecurely held therein.

Therefore, in the first embodiment, the nut element ($n$) is screwed in the protruded screw portion (12) of the implant screw pin ($i$) until the underside (base portion) of the nut element ($n$) is pressed to contact with the surface of the jaw bone ($b$), i.e., an upperside hard tissue ($b_1$). The implant screw pin ($i$), which is anchored after screwed in the jaw bone ($b$), is then pulled upward by the tightening of the nut element ($n$), whereupon the external threading of the screw ($l$) and internal threading of the tapped hole (5) are tightly abutted. Thus, the implant screw pin ($i$) is tightly secured to the jaw bone ($b$) even under repeated biting stresses. Next, an artificial tooth ($t$) is fixed into the uppermost portion of the nut element ($n$). At this stage, in order to prevent rotation of the nut element ($n$) and also to connect the nut element ($n$) to the artificial tooth ($t$), an adhesive compound (4), such as cement or amalgam, is filled between a fixing hole ($t_1$) grooved in a tooth neck ($t_2$) and the top of the nut element ($n$). The artificial tooth ($t$) is secured to the nut element ($n$) by pressing or striking the tooth on its upper surface. In this case, the adhesive compound (4) preferably fills an internal space (3) so that no voids or vacancies are left therein. the implant As shown in FIG. 2, it is preferable to provide a facing shoulder (6) for pressing the underside of the nut element ($n$) onto the upperside hard bone tissue ($b_1$) around the tapped hole (5). Facing shoulder (6) prevents lateral loosening of the nut element ($n$). In the heretofore described structural relation in FIG. 2, the implant screw pin is used with the length as fabricated; however, the thickness of the jaw bone ($b$) differs with one patient to another so that there are some cases where the relationship between the length of the implant screw pin ($i$) and the thickness of the jaw bone ($b$) is not precisely as presented in FIG. 2. In a case where the jaw bone ($b$) is excessively thin, the excess portion of the implant screw pin ($i$) [and a part of the nut element ($n$)] is severed by a tool so that the imlant screw pin ($i$) may be properly inserted in the jaw bone ($b$) in the relationship as shown in FIG. 2. Accordingly, in the first embodiment, the length of the ready-made implant screw pin ($i$) should be preferably substantially larger than the average thickness of the jaw bone ($b$) so as to be properly severed at the latter stage. Alternatively, a cap nut (not shown) could be used for the nut element ($n$) in the above embodiment. In that case, an adhesive compound is filled in the inner space of the cap nut prior to threading into the implant screw pin ($i$). It is desirable to have the lowermost end of the implant screw pin ($i$) stepped into the hard tissue ($b_3$) so that implant screw pin ($i$) is well secured. Nevertheless, even if the lowermost end of the implant screw pin ($i$) is stopped within a soft tissue ($b_2$), it is also possible in the first embodiment to obtain tight screwing connection with the provision of the nut element ($n$). The adhesive compound (4) may be avoided in the case where the artificial tooth ($t$) and the nut element ($n$) are tightly fixed together.

Figure 3:
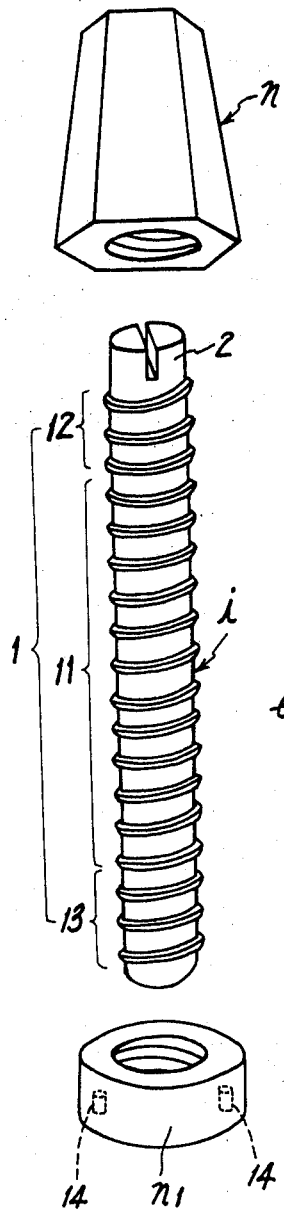
FIG. 3 is a perspective view of a device for implanting an artificial endosseous element according to the second embodiment of the invention.
Figure 4:
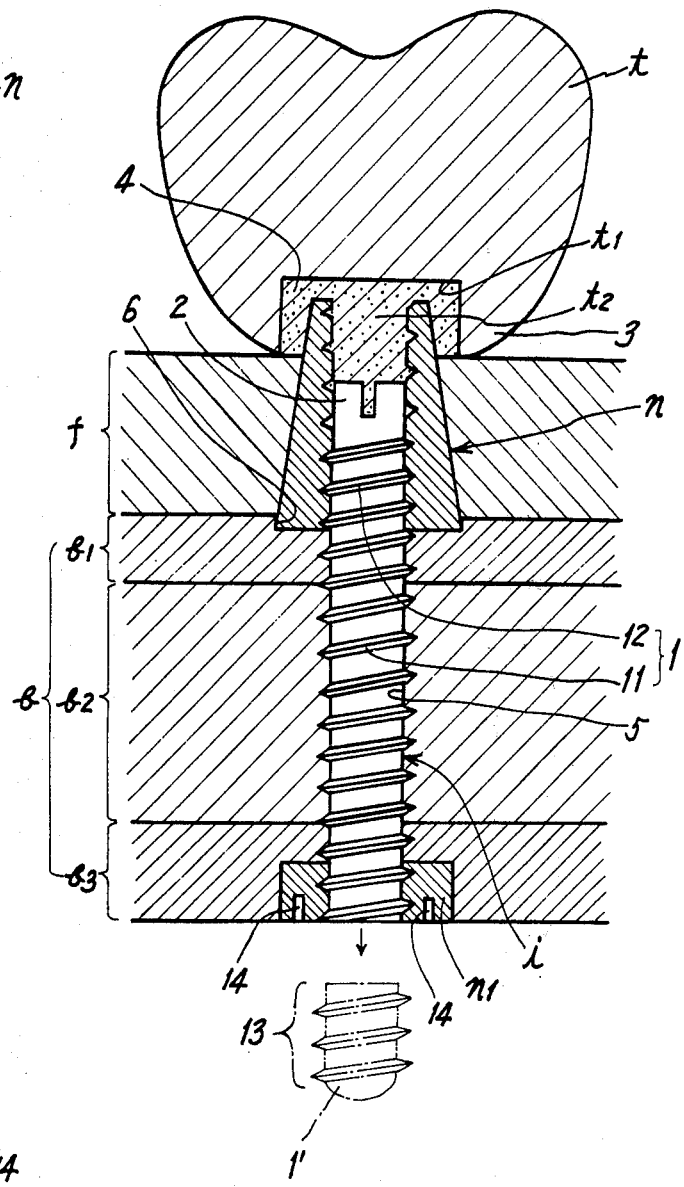
FIG. 4 is a cross-sectional view showing the implantation of an artificial tooth of the type illustrated in FIG. 3.
Figure 5:
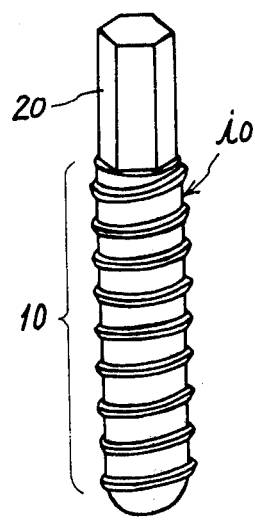
FIG. 5 is a perspective view of a conventional implant screw pin.
Figure 6:
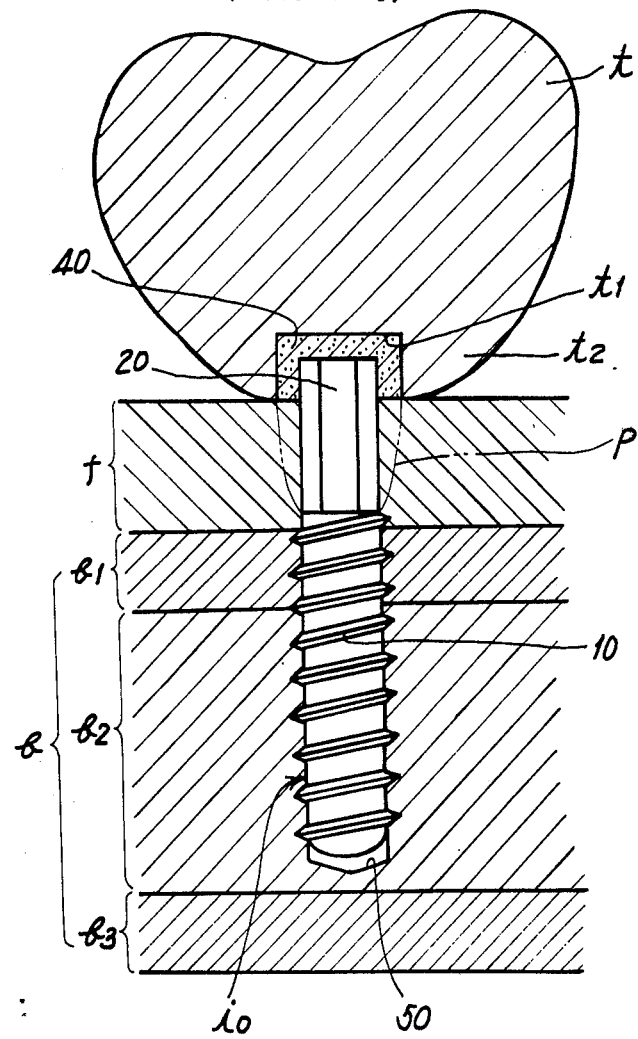
FIG. 6 is a cross-sectional view showing the implantation of an artificial tooth of the implant screw pin type of FIG. 5.

The second embodiment is shown in FIGS. 3 and 4, in which FIG. 3 shows a perspective view of an implant screw pin and a nut element according to the second embodiment, and FIG. 4 shows a cross section illustrating the implantation of the artificial tooth using the implant screw pin and the nut element shown in FIG. 3. The essential difference of the implant element in the first embodiment and the second embodiment resides in the use of an auxiliary nut element. The additional provision of the auxiliary nut element also produces a substantial difference in the implantation technique, since in the second embodiment, the implant screw pin is secured from both upper and lower portions of the jaw bone after the implant has penetrated through the jaw bone. By this procedure, the rigidity and durability of the implant screw pin can be further increased. This advantage is detailed in the following. An auxiliary nut element ($n_1$), which is shown as a cylindrical shape in the drawing, is a ceramic nut which is screwed onto the lower protruded screw portion (13) of the implant screw pin ($i$) which penetrates through the jaw bone ($b$). The upper surface of the auxiliary nut element ($n_1$) is tightly secured against the lowermost surface of the jaw bone ($b$). The prosthesis of an artificial tooth ($t$) using the elements of the second embodiment is described by way of FIG. 4. A gingival tissue ($f$) of the prosthesis section is incised and a tapped hole (5), corresponding with a main screw portion (11) of the implant screw pin ($i$), is provided through the jaw bone ($b$). A screwdriver is attached to a slotted attaching portion (2) and the implant screw pin rotated so that a screw (1) is screwed in the tapped hole (5) with a lower end of the screw (1) protruding from the lower hard tissue ($b_3$) of the jaw bone ($b$) to form a protruded screw portion (13). Onto the lowermost end of the protruded screw portion (13), the above-mentioned auxiliary nut element ($n_1$) is screwed onto the implant screw pin ($i$) which penetrates through the jaw bone ($b$).

Then in the same manner as the prior embodiment, the nut element ($n$) is screwed onto the protruded screw portion (12) of the implant screw pin ($i$) so that the nut element ($n$) and the above-mentioned auxiliary nut element ($n_1$) are pressed into contact with the hard tissue ($b_1$) and ($b_3$) respectively of the upper and lower sides of the jaw bone. By this procedure, the implant screw pin ($i$) is double locked from both ends of the screw pin and tensioned from both ends, thereby securing the screw pin in the jaw bone ($b$) even under repeated biting stresses.

The manner in which an artificial tooth ($t$) is fixed into the nut element ($n$) through the adhesive compound (4) is the same as that of the first embodiment. It is also desired to provide a facing shoulder (7) in the hard tissue ($b_3$) for the auxiliary nut element ($n_1$) as was the case for the nut element ($n$). The upperside of the auxiliary nut element ($n_1$) may then be pressed in the facing shoulder (7) not only to assure stability of the auxiliary nut element ($n_1$), but also to avoid surgical awkwardness or internal extraordinary growth of the tissues due to the protrusion of foreign substance at the lowerside of the jaw bone ($b$). It is preferable to provide apertures (14) for attaching a tool for rotating the auxiliary nut ($n_1$) in the top surface thereof in order to easily screw the auxiliary nut into the facing shoulder (7).

The advantages of the second embodiment, in which the implant screw pin ($i$) is double locked by two nut elements are that the resistance to biting stresses is further increased, and that the unpleasant feeling which would be caused by the protrusion of the lower portion of the implant screw pin ($i$) is removed. Furthermore, in the second embodiment, severing of the fabricated implant screw pin ($i$) after implantation can be made at the lowerside thereof, i.e., at the lowerside of the hard tissue ($b_3$) and therefore, the fixed relationship among the upperside of the implant screw pin ($i$), the nut element ($n$) and the artificial tooth ($t$) may be preserved. In other words, in the first embodiment, the upperside of the implant screw pin, including part of the nut element, has to be, in some cases, severed while on the other hand the implant screw pin ($i$) in the second embodiment has to be severed only at the lowerside thereof (see numeral 1′ in FIG. 4). Accordingly, in the latter embodiment, it is easy not only to sever the screw pin but also to produce fixed implant which includes the nut element ($n$). This is accomplished by fabricating the implant screw pin in substantial lengths in order to permit severance at the lower side thereof.

As has been described in two preferred embodiments of the invention, the artificial tooth ($t$) and the implant screw pin ($i$) are not directly connected, but the implant screw pin ($i$) threaded in the jaw bone ($b$) is tightened by means of a nut element for securing implant screw pin ($i$) in the jaw bone. Next, the tooth neck ($t_2$) of the artificial tooth ($t$) is fixed directly or through an adhesive compound (4) onto the nut element. Thus, the implanted artificial tooth can endure the repeated biting stresses imparted by the tooth neck ($t_2$) by virtue of the nut and implant screw pin construction. When the biting stress is transmitted to the implant screw pin ($i$) through the nut element ($n$), the implant screw pin ($i$) is tightly secured to the nut element ($n$), and retains its integrity without loosening.

Furthermore, in this invention, as seen from the second embodiment, by use of the two nut elements at both ends of the implant screw pin, the above functions of this invention as heretofore described is promoted and dental implantation is facilitated.

Accordingly, the growth of the tissues surrounding the implant screw pin after prosthesis is excellent in the present invention and also the bone atrophy due to unstability of the implant screw pin is substantially removed, thereby avoiding infection of bacilli or pocket formation which causes loss of the implant which was common in the prior art.

As for the implant element material, ceramics is preferred since it is compatible with the bone tissue and is nontoxic. Nor does it become a subsidiary cause of disease, even if the implant is left in place for a long period after implantation. Furthermore, ceramic is durable and rigid even over long periods of use.

The implant element is described hereinbefore with respect to the fields of dentistry and oral surgery. However, this invention should not be limited to the above fields since this invention also obtains the above advantages in the field of orthopedics, and in particular the prosthesis of arms, legs and the like.

We claim:

1. A device for implanting an artificial endosseous element containing:

an implant screw pin, said pin being of a radio opaque ceramic and having an external threading, said pin including a portion to be threaded into a bone structure and a protruded portion to be protruded from the upper surface of said bone structure when said pin is threaded into the bone structure, said pin being provided with a tool-attaching portion at the top of said protrusion, and a nut element made of ceramic, said nut element being substantially larger in diameter than said pin, said nut element being threaded onto said protruded portion of said pin until the underside of said nut element engages with the upper surface of said bone structure thereby tightly holding said pin in said bone structure.

2. The device for implanting an artificial endosseous element according to claim 1, wherein said threading of the pin is a single screw thread provided from said portion to be threaded into the bone structure to said protruded portion to be protruded from the upper surface of the bone structure.

3. The device for implanting an artificial endosseous element according to claim 1, wherein the length of said pin is substantially longer than the thickness of said bone structure in which said pin is threaded so that said tool-attaching portion may be severed from said pin leaving said protruded portion of said screw after said pin is threaded into said bone structure.

4. The device for implanting an artificial endosseous element according to claim 1, wherein the external circumference of said nut element is tapered so as to be smaller at the top of said nut element than at the bottom of said nut element.

5. The device for implanting an artificial endosseous element according to claim 1, wherein said tool-attaching portion is of a hexagonal pillar shape.

6. The device for implanting an artificial endosseous element according to claim 1, wherein said tool-attaching portion is of a pillar shape having a groove therein.

7. The device for implanting an artificial endosseous element according to claim 1, wherein said implant screw pin and said nut element being made respectively of a burnt ceramic composition of matter consisting substantially of 95 to 50% of $Al_2O_3$ and 5 to 50% of more than one compound selected from the group consisting of $ZrO_2$, $La_2O$ and $Y_2O_3$.

8. The device for implanting an artificial endosseous element according to claim 1, wherein said implant screw pin and said nut element being made respectively of a burnt ceramic composition of matter consisting substantially of 90 to 80% of $Al_2O_3$ and 10 to 20 % of more than one compound selected from the group consisting of $ZrO_2$, $La_2O$ and $Y_2O_3$.

9. A method of implanting an artificial endosseous element into a bone structure of a human body for restoring said bone structure to its original configuration containing the steps of:
  forming a tapped hole in said bone structure;
  screwing into said tapped hole an externally threaded implant screw pin of ceramics until the upper portion of said pin is below the top surface of the gingival tissue and protrudes from said bone structure and until the bottom of said pin is in hard tissue at the lower side of said bone structure; and
  screwing a nut element of ceramics onto said protruded portion of said pin until the underside of said nut element engages with the upper surface of said bone structure to tightly hold said pin in said bone structure.

10. The method of implanting an artificial endosseous element into a bone structure of a human body for restoring said bone structure to its original configuration according to claim 9, wherein a step of forming a facing shoulder around said tapped hole in hard tissue of the upper side of said bone structure is further included.

11. A method of implanting artificial dental endosseous element into a bone structure of a human jaw for restoring said bone structure to its original configuration containing the steps of:
  forming a tapped hole in said bone structure;
  screwing into said tapped hole an externally threaded implant screw pin of ceramics until the upper portion of said pin is below the top surface of the gingival tissue and protrudes from said bone structure and until the bottom of said pin is in hard tissue at the lower side of said bone structure;
  screwing a nut element of ceramics onto said protruded portion of said pin until the underside of said nut element engages with the upper surface of said bone structure to tightly hold said pin in said bone structure; and
  securely fixing an artificial tooth to said nut element through an adhesive compound.

12. A device for implanting an artificial endosseous element containing:
  an implant screw pin, said pin being of ceramics and having an external threading, said pin including a portion to be threaded in a bone structure in an upper and lower protruded portion to protrude from the upper and lower surfaces of said bone structure when said pin is screwed into said bone structure, said pin being provided with a tool attaching portion at the bottom thereof,
  a first nut element, said first nut element being screwed onto the lower protruded portion of said screw,
  a second nut element, said second nut element being substantially larger in diameter than said pin, said second nut element being screwed onto the upper protruded portion until the underside of said nut element engages with the upper surface of said bone structure thereby holding said pin in said bone structure.

13. The device for implanting an artificial endosseous element according to claim 12, wherein said threading of the pin is a single screw thread provided from said portion to be threaded into the bone structure to said upper and lower protruded portions to protrude from the upper and lower surfaces of the bone structure.

14. The device for implanting an artificial endosseous element according to claim 12, wherein the length of said pin is substantially longer than the thickness of said bone structure in which said pin is threaded so that said tool-attaching portion may be severed from said pin leaving said upper and lower protruded portions of said screw after said pin is screwed in said bone structure.

15. The device for implanting an artificial endosseous element according to claim 12, wherein the external circumference of said upper nut element is tapered so as to be smaller at the top of said nut element than at the bottom of said nut element.

16. The device for implanting an artificial endosseous element according to claim 12, wherein said tool-attaching portion is of a hexagonal pillar shape.

17. The device for implanting an artificial endosseous element according to claim 12, wherein said tool-attaching portion is of a pillar shape having a groove therein.

18. The device for implanting an artificial endosseous element according to claim 12, wherein said implant screw pin and said nut elements being made respectively of a burnt ceramic composition of matter consisting substantially of 95 to 50% of $Al_2O_3$ and 5 to 50% of more than one compound selected from the group consisting of $ZrO_2$, $La_2O$ and $Y_2O_3$.

19. The device for implanting an artificial endosseous element according to claim 12, wherein said implant screw pin and said nut elements being made respectively of a burnt ceramic composition of matter consisting substantialy of 90 to 80% of $Al_2O_3$ and 10 to 20% of more than one compound selected from the group consisting of $ZrO_2$, $La_2O$ and $Y_2O_3$.

20. A method of implanting an artificial endosseous element into a bone structure of a human body for restoring said bone structure to its original configuration containing the steps of
  forming a single tapped hole penetrating throughout said bone structure;
  screwing into said tapped hole an externally threaded implant screw pin of ceramics so as to permit an upper and lower portion of said screw of the pin to be upwardly and downwardly protruded from said bone structure;
  screwing a first nut element of ceramics onto said lower protruded portion; and screwing a second nut element of ceramics onto said upper protruded portion of said pin until said lower surface of said second nut element engages with the upper surface of said bone structure thereby tightly holding said pin in said bone structure.

21. The method of implanting an artificial endosseous element into a bone structure of a human body for restoring said bone structure to its original configuration according to claim 20, wherein a step of forming an upper and lower facing shoulder around said tapped hole in the hard tissues respectively of the upper and lower sides of said bone structure is further included.

22. A method of implanting an artificial dental endosseous element into a bone structure of a human jaw for restoring said bone structure to its original configuration comprising:

forming a tapped hole penetrating through said bone structure;

screwing into said tapped hole an externally threaded implant screw pin of ceramics so as to permit an upper and lower portion of said threading of said pin respectively to be upwardly and downwardly protruded from said bone structure;

screwing a first nut element of ceramics onto said lower protruded portion; screwing a second nut element of ceramics onto said upper protruded portion of said pin until the lower surface of said second nut element engages with the upper surface of said bone structure thereby tightly holding said pin in said bone structure; and securely fixing an artificial tooth to said upper nut element through an adhesive compound.

* * * * *